United States Patent
Benage et al.

(10) Patent No.: US 6,660,181 B2
(45) Date of Patent: Dec. 9, 2003

(54) INHIBITION OF POLYMERIZATION OF UNSATURATED MONOMERS

(75) Inventors: Brigitte Benage, Wolcott, CT (US); Angela M. Edwards, Naugatuck, CT (US); Vilen Kosover, Cheshire, CT (US); Gan Wang, Wallingford, CT (US); Anthony Gentile, Waterbury, CT (US); Jesus R. Fabian, Wethersfield, CT (US); Gerald J. Abruscato, Southington, CT (US)

(73) Assignee: Crompton Corporation, Middlebury, CT (US)

(*) Notice: Subject to any disclaimer, the term of this patent is extended or adjusted under 35 U.S.C. 154(b) by 0 days.

(21) Appl. No.: 10/193,603

(22) Filed: Jul. 12, 2002

(65) Prior Publication Data

US 2003/0080318 A1 May 1, 2003

Related U.S. Application Data

(63) Continuation-in-part of application No. 09/453,099, filed on Dec. 2, 1999, now abandoned.

(51) Int. Cl.[7] .................................................. C09K 3/00
(52) U.S. Cl. ...................... 252/183.12; 252/401; 585/4; 585/5; 585/832
(58) Field of Search ................................ 585/4, 5, 832; 252/183.12, 401

(56) References Cited

U.S. PATENT DOCUMENTS 3,163,677 A  12/1964  Hoffman et al. ............ 260/583
3,253,055 A   5/1966  Goble et al. ........... 260/638.75

(List continued on next page.)

FOREIGN PATENT DOCUMENTS

CZ   260755 B1 890515    1/1989
EP       0 178 168 A2   10/1985

(List continued on next page.)

OTHER PUBLICATIONS

Wang et al., Lanzhou Daxue Xuebao, Ziran Kexueban 23(3):138–140 (1987).

Primary Examiner—Cephia D. Toomer
(74) Attorney, Agent, or Firm—Michael P. Dilworth; Paul Grandinetti (57) ABSTRACT

A method is disclosed for inhibiting the premature polymerization of ethylenically unsaturated monomers comprising adding to said monomers a polymerization inhibiting amount of a mixture comprising A) a first inhibitor comprising 4-amino-2,2,6,6-tetramethylpiperidinyloxy, wherein said amino group is a primary, secondary, or tertiary amino group; and B) at least one other inhibitor having the structural formula:

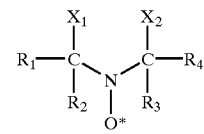

wherein:

$R_1$ and $R_4$ are independently selected from the group consisting of hydrogen, alkyl, and heteroatom-substituted alkyl;

$R_2$ and $R_3$ are independently selected from the group consisting of alkyl and heteroatom-substituted alkyl;

$X_1$ and $X_2$ (1) are independently selected alkyl groups of 1 to 15 carbon atoms or (2) taken together, form a ring structure with the nitrogen.

17 Claims, 3 Drawing Sheets

U.S. PATENT DOCUMENTS

| | | | |
|---|---|---|---|
| 3,334,103 A | 8/1967 | Feldman et al. | 260/290 |
| 3,372,182 A | 3/1968 | Hoffmann et al. | 260/465.5 |
| 3,422,144 A | 1/1969 | Hoffman et al. | 260/570 |
| 3,494,930 A | 2/1970 | Dupeyre et al. | 260/294.7 |
| 3,502,692 A | 3/1970 | Feldman et al. | 260/326.3 |
| 3,704,233 A | 11/1972 | Eich et al. | 260/285.5 |
| 3,747,988 A | 7/1973 | Bailey | 203/8 |
| 3,873,564 A | 3/1975 | Schneider et al. | 260/309.6 |
| 3,966,711 A | 6/1976 | Rasberger | 260/239.9 |
| 4,182,658 A | 1/1980 | Watson | 203/9 |
| 4,665,185 A | 5/1987 | Winter et al. | 546/184 |
| 5,254,760 A | 10/1993 | Winter et al. | 585/435 |
| 5,545,782 A | 8/1996 | Winter et al. | 585/435 |
| 5,545,786 A | 8/1996 | Winter et al. | 585/435 |
| 5,728,872 A | 3/1998 | Riemenschneider | 562/598 |
| 5,877,344 A | 3/1999 | Gande et al. | 560/205 |
| 6,117,276 A | 9/2000 | Cunkle et al. | 203/8 |
| 6,200,460 B1 | 3/2001 | Sutoris et al. | 208/48 |
| 6,300,533 B1 | 10/2001 | Benage et al. | 585/5 |

FOREIGN PATENT DOCUMENTS

| | | |
|---|---|---|
| EP | 0 765 856 A1 | 4/1997 |
| FR | 2761060 | 8/1999 |
| GB | 1127127 | 4/1966 |
| RU | 478838 | 7/1975 |
| RU | 334845 A1 | 1/1984 |
| WO | 97/46504 | 12/1997 |
| WO | 98/02403 | 1/1998 |
| WO | WO 98/14416 | 4/1998 |
| WO | 98/25872 | 6/1998 |

Figure 3
Feed Shut-Off Curves for DMATEMPO

INHIBITION OF POLYMERIZATION OF UNSATURATED MONOMERS

CROSS REFERENCE TO RELATED APPLICATION

This is a continuation-in-part of U.S. application Ser. No. 09/453,099, filed Dec. 2, 1999, now abandoned.

BACKGROUND OF THE INVENTION

1. Field of the Invention

The present invention is directed to the use of a combination of at least two stable nitroxide free radical compounds to inhibit the polymerization of ethylenically unsaturated monomers.

2. Description of Related Art

Many ethylenically unsaturated monomers undesirably polymerize at various stages of their manufacture, processing, handling, storage, and use. A particularly troublesome problem is equipment fouling caused by polymerization in the purification stages of the production processes of such monomers. Polymerization, such as thermal polymerization, during their purification results in the loss of the monomer and a loss in production efficiency owing to the deposition of polymer in or on the equipment being used in the purification, the deposits of which must be removed from time to time. Additionally, the formation of soluble polymer leads to loss of monomer, i.e., a lower yield, and an increase in the viscosity of any tars that may be produced. The processing of the tars then requires higher temperature and work (energy cost) to remove residual monomer.

A wide variety of compounds has been proposed and used for inhibiting uncontrolled and undesired polymerization of ethylenically unsaturated monomers. However, these compounds have not been fully satisfactory. Accordingly, there has been a substantial need in the art for improved compositions for inhibiting the polymerization of such monomers during their production and the distillation process for purifying or separating them from impurities, as well as during transport and storage.

Hindered nitroxyl compounds are known to be very active inhibitors of free radical polymerizations of unsaturated monomers such as styrene, acrylic acid, methacrylic acid, and the like.

U.S. Pat. No. 3,163,677 discloses N,N,O-trisubstituted hydroxylamines and N,N-disubstituted nitroxides of the formulae:

wherein $R_1$, $R_2$, and $R_3$ are each an alkyl radical having 1 to 15 carbon atoms. (As used herein, the designation N—O* denotes a stable free radical wherein the asterisk is an unpaired electron.) The N,N,O-trisubstituted hydroxylamines can be used to make the N,N-disubstituted nitroxides, which are stable free radicals and are said to be useful as polymerization inhibitors.

U.S. Pat. No. 3,334,103 discloses that nitroxides can be prepared from the corresponding heterocyclic amine wherein the nitrogen atom of the nitroxide group is attached to other than a tertiary carbon of an aliphatic group (i.e., the nitrogen atom forms a part of a heterocyclic nucleus). These nitroxides are said to have useful properties similar to those described for the N,N-disubstituted nitroxides of U.S. Pat. No. 3,163,677.

U.S. Pat. No. 3,372,182 discloses that a great variety of N,N-disubstituted, stable, free radical nitroxides not otherwise readily available can be prepared by a simple and convenient process that comprises pyrolyzing in an inert reaction medium virtually any hydroxylamine that is susceptible to cleavage of the O—C bond, e.g., tri-t-butylhydroxylamine.

U.K. Patent Number 1,127,127 discloses that acrylic acid can be stabilized against polymerization by the addition thereto of a nitroxide having the essential skeletal structure:

wherein $R_1$, $R_2$, $R_3$, and $R_4$ are alkyl groups and no hydrogen is bound to the remaining valencies on the carbon atoms bound to the nitrogen. The two remaining valencies that are not satisfied by $R_1$ to $R_4$ or nitrogen can also form part of a ring (e.g., 2,2,6,6 tetramethyl-4-hydroxy-piperidine-1-oxyl).

U.S. Pat. No. 3,422,144 discloses stable, free radical nitroxides of the formula:

wherein R is selected from the group consisting of tertiary alkyl, aryl, alkaryl, haloaryl, carboxyaryl, alkoxyaryl, alkylthioaryl, pyridyl, and dialkylaminoaryl, and R' is tertiary alkyl. These nitroxides are said to be useful as traps for reactive free radicals both in the counting of free radicals and for inhibiting oxidation and free radical polymerization.

U.S. Pat. No. 3,494,930 discloses free radicals of the nitroxide type for use as initiators of free radical reactions, collectors of free radicals, polymerization inhibitors or antioxidants. They are constituted by nitrogenous bicyclic compounds in which one of the bridges comprises solely the nitroxide radical group and, in particular, by aza-9-bicyclo (3,3,1) nonanone-3-oxyl-9, and by aza-9-bicyclo (3,3,1) nonane oxyl-9.

U.S. Pat. No. 3,873,564 discloses compounds and a method for assaying enzymes by adding to a medium containing an enzyme a stable free radical compound having a stable free radical functionality which, when subjected to an enzyme-catalyzed reaction, changes the environment of the free radical functionality. By following the change in the electron spin resonance spectrum as affected by the change in environment, the type of enzyme and the activity of the enzyme can be determined.

The compounds found useful are normally stable nitroxide radicals with an enzyme labile functionality. Other compounds include two cyclic nitroxide containing rings joined by a chain having an enzyme labile functionality.

U.S. Pat. No. 3,966,711 teaches that 2,2,7,7-tetraalkyl- and 2,7-dispiroalkylene-5-oxo-1,4-diazacycloheptanes substituted in the 4-position by mono- or tetravalent radicals are powerful light-stabilizers for organic polymers They are said to possess higher compatibility than their 4-unsubstituted homologues, from which they can be synthesized by reactions known for N-alkylation. Preferred substituents in the 4-position are alkyl, alkylene, alkenyl, aralkyl, and esteralkyl groups. The 1-nitroxyls derived from the imidazolidines by oxidation with hydrogen peroxide or percarboxylic acids are also said to be good light stabilizers.

U.S. Pat. No. 4,182,658 discloses a method for preventing the polymerization of a readily polymerizable vinyl aromatic compound during distillation at elevated temperatures within a distillation apparatus that is subject to an emergency condition, such as a power outage. This method comprises force-feeding a supplemental polymerization inhibitor having a high solubility in the vinyl aromatic compound and a long duration of efficiency into each of the distillation vessels of a conventional distillation apparatus in an amount sufficient to prevent polymerization therein.

European Patent Application 0 178 168 A2 discloses a method for inhibiting the polymerization of an α,β-ethylenically unsaturated monocarboxylic acid during its recovery by distillation by using a nitroxide free radical.

U.S. Pat. No. 4,665,185 discloses a process for the efficient preparation of nitroxyls of sterically hindered amines by the oxidation of the amine using a hydroperoxide in the presence of a small amount of a metal ion catalyst, at moderate temperature for a short period of time, to give the nitroxyl in high yield and purity.

U.S. Pat. No. 5,254,760 teaches that the polymerization of a vinyl aromatic compound, such as styrene, is very effectively inhibited during distillation or purification by the presence of at least one stable nitroxyl compound together with at least one aromatic nitro compound.

U.S. Pat. Nos. 5,545,782 and 5,545,786 disclose that nitroxyl inhibitors in combination with some oxygen reduce the premature polymerization of vinyl aromatic monomers during the manufacturing processes for such monomers. Even small quantities of air used in combination with the nitroxyl inhibitors are said to result in vastly prolonged inhibition times for the monomers.

U.S. Pat. No. 6,136,951 discloses a method for evaluating the polymer growth inhibition ability of a compound or compounds wherein the method comprises: A) weighing a dry seed of insoluble polymer capable of growing via a living polymerization mechanism; B) subjecting the seed of insoluble polymer to conditions capable of causing a living polymer to grow via a living polymerization mechanism; C) drying the seed; and D) weighing the seed a second time to determine any increase in weight; wherein the polymer growth inhibition ability of the compound or compounds is inversely proportional to any increase found in weight of the seed.

U.S. Pat. No. 6,274,683 discloses an improvement in a method for evaluating the efficiency of polymerization inhibitors, wherein the improvement comprises: A) producing dissolved polymer in a solution comprising monomer and at least one inhibitor by means of any test known in the art to be useful for evaluating polymerization inhibitors, B) collecting the polymer-containing solution, C) measuring the degree of polymerization of the monomer in the collected solution, and D) re-subjecting the polymer-containing solution to the test conditions of A).

U.S. Pat. No. 6,300,533 discloses a method for inhibiting the premature polymerization of ethylenically unsaturated monomers comprising adding to said monomers an effective amount of an inhibitor having the structural formula:

wherein $R_1$ and $R_4$ are independently selected from the group consisting of hydrogen, alkyl, and heteroatom-substituted alkyl and $R_2$ and $R_3$ are independently selected from the group consisting of alkyl and heteroatom-substituted alkyl and the portion represents the atoms necessary to form a five-, six-, or seven-membered heterocyclic ring, at least one of said atoms being a carbon atom substituted with a primary, secondary, or tertiary amino group.

U.S. Pat. No. 6,344,560 discloses the use of a nitroaromatic compound to enhance the solubility of a nitroxyl compound in an aromatic hydrocarbon solvent.

U.S. Pat. No. 6,403,850 discloses a method for inhibiting the premature polymerization of ethylenically unsaturated monomers comprising adding to said monomers an effective amount of A) at least one stable hindered nitroxyl compound having the structural formula:

wherein $R_1$ and $R_4$ are independently selected from the group consisting of hydrogen, alkyl, and heteroatom-substituted alkyl and $R_2$ and $R_3$ are independently selected from the group consisting of alkyl and heteroatom-substituted alkyl; and $X_1$ and $X_2$ (1) are independently selected from the group consisting of halogen, cyano, $COOR_7$, $—S—COR_7$, $—OCOR_7$, (wherein $R_7$ is alkyl of 1 to 15 carbon atoms, or (2) taken together, form a ring structure with the nitrogen; and B) at least one phenylenediamine, and, optionally, C) at least one nitroaromatic compound.

European Patent Application 0 765 856 A1 discloses a stabilized acrylic acid composition in which the polymerization of the acrylic acid is inhibited during the distillation process for purifying or separating the acrylic acid as well as during transport and storage. The compositions comprise three components: (a) acrylic acid, (b) a stable nitroxyl radical, and (c) a dihetero-substituted benzene compound having at least one transferable hydrogen (e.g., a quinone derivative such as the monomethyl ether of hydroquinone (MEHQ)). During the distillation process, transport, and storage, components (b) and (c) are present in a polymerization-inhibiting amount. During the distillation process, oxygen (d) is preferably added with components (b) and (c). According to the specification, examples of suitable nitroxide free radical compounds include di-t-butylnitroxide; di-t-amylnitroxide; 2,2,6,6-tetramethyl-piperidinyloxy; 4-hydroxy-2,2,6,6-tetramethyl-piperidinyloxy; 4-oxo-2,2,6,6-tetramethyl-piperidinyloxy; 4-dimethylamino-2,2,6,6-tetramethyl-piperidinyloxy; 4-amino-2,2,6,6-tetramethyl-piperidinyloxy;

4-ethanoyloxy-2,2,6,6-tetramethyl-piperidinyloxy; 2,2,5,5-tetramethylpyrrolidinyloxy; 3-amino-2,2,5,5-tetramethylpyrrolidinyloxy; 2,2,5,5-tetramethyl-1-oxa-3-azacyclopentyl-3-oxy; 2,2,5,5-tetramethyl-1-oxa-3-pyrrolinyl-1-oxy-3-carboxylic acid; and 2,2,3,3,5,5,6,6-octamethyl-1,4-diazacyclohexyl-1,4-dioxy.

WO 97/46504 concerns substance mixtures containing: (A) monomers containing vinyl groups; and (B) an active amount of a mixture which inhibits premature polymerization of the monomers containing vinyl groups during their purification or distillation and contains: (i) between 0.05 and 4.5 wt %, relative to the total mixture (B), of at least one N-oxyl compound of a secondary amine which has no hydrogen atom at the α-C atoms; and (ii) between 99.95 and 95.5 wt % relative to the total mixture (B), of at least one nitro compound. The publication also discloses a process for inhibiting the premature polymerization of monomers, and the use of mixture (B) for inhibiting the premature polymerization of monomers.

WO 98/02403 relates to inhibiting the polymerization of vinyl aromatic compounds by using a mixture of a phenol and a hydroxylamine. It is said that the process is useful in ethylbenzene dehydrogenation effluent condenser systems and styrene-water separator vent gas compressor systems and that it effectively inhibits polymerization of monomers, preventing the formation of a polymer coating on condenser and compressor equipment, thus reducing the necessity for cleaning of equipment surfaces.

WO 98/14416 discloses that the polymerization of vinyl aromatic monomers such as styrene is inhibited by the addition of a composition of a stable hindered nitroxyl radical and an oxime compound.

WO 98/25872 concerns substance mixtures containing (A) compounds containing vinyl groups; (B) an active amount of a mixture which inhibits premature polymerization of the compounds containing vinyl groups and contains: (i) at least one N-oxyl compound of a secondary amine which does not carry any hydrogen atoms on the α-carbon atoms; and (ii) at least one iron compound; (C) optionally nitro compounds; and (D) optionally co-stabilizers. The publication also discloses a process for inhibiting the premature polymerization of compounds (A) containing vinyl groups, and the use of (B) optionally mixed with nitro compounds (C) and/or co-stabilizers (D) for inhibiting the premature polymerization of radically polymerizable compounds and stabilizing organic materials against the harmful effect of radicals.

CS-260755 B1 is directed to the preparation of 4-substituted-2,2,6,6-tetramethylpiperidine nitroxyls as olefin stabilizers.

SU-334845 A1 is directed to the inhibition of the radical polymerization of oligoester acrylates using iminoxyl radical inhibitors of a given formula.

SU-478838 is directed to the inhibition of the radical polymerization of oligoester acrylates and the prevention of oligomeric peroxides using a binary polymerization inhibitor comprising quinone.

FR 2,761,060 relates to the prevention of premature polymerization of styrene during its production by dehydrogenation of ethylbenzene by injecting into the process effluent a radical inhibitor based on an oxyl-tetramethylpiperidine derivative.

Wang et al., Lanzhou Daxue Xuebao, Ziran Kexueban 23(3): 138–140 (1987) evaluated the inhibition effect of the stable nitroxide free radical, di-t-butylnitroxide, on the polymerization of acrylic acid and styrene monomers by three methods: separation method, reboiling method, and expanding method. The results showed that di-t-butylnitroxide itself has an inhibiting effect, and when it blends with hydroquinone, t-butyl catechol, benzoquinone, the inhibition effect is better than common inhibitors.

The foregoing are incorporated herein by reference in their entirety.

SUMMARY OF THE INVENTION

As used herein, the abbreviation TEMPO stands for 2,2,6,6-tetramethyl-1-piperidinyloxy. Thus, 4-amino-TEMPO is 4-amino-2,2,6,6-tetramethyl-1-piperidinyloxy; 4-hydroxy-TEMPO is 4-hydroxy-2,2,6,6-tetramethyl-1-piperidinyloxy (also known in the art as HTEMPO); 4-oxo-TEMPO is 4-oxo-2,2,6,6-tetramethyl-1-piperidinyloxy; and so on. As used herein, unless specified otherwise, the amino group of 4-amino-TEMPO can be primary, secondary, or tertiary, e.g., 4-amino-2,2,6,6-tetramethyl-1-piperidinyloxy, 4-(N-alkylamino)-2,2,6,6-tetramethyl-1-piperidinyloxy, or 4-(N,N-dialkylamino)-2,2,6,6-tetramethyl-1-piperidinyloxy.

As mentioned above, hindered nitroxyl compounds are known to be very active inhibitors of free radical polymerizations of unsaturated monomers. The present invention is directed to the discovery that a mixture of at least two stable hindered nitroxyl compounds (e.g., 4-amino-TEMPO and 4-oxo-TEMPO) provides better performance than an equivalent charge of either component alone, as indicated by the slow rate of polymerization after shutoff of feed in a steady state dynamic testing system.

More particularly, the present invention is directed to a method for inhibiting the premature polymerization of ethylenically unsaturated monomers comprising adding to said monomers an effective amount of a mixture comprising at least two different inhibitors having the following structural formula:

In this formula, $R_1$ and $R_4$ are independently selected from the group consisting of hydrogen, alkyl, and heteroatom-substituted alkyl and $R_2$ and $R_3$ are independently selected from the group consisting of alkyl and heteroatom-substituted alkyl; and $X_1$ and $X_2$ (1) are independently selected from the group consisting of halogen, cyano, $COOR_9$ (wherein $R_9$ is alkyl or aryl), amido, —S—$C_6H_5$, —S—$COCH_3$, —$OCOC_2H_5$, carbonyl, alkenyl, or alkyl of 1 to 15 carbon atoms, or (2) taken together, form a ring structure with the nitrogen, preferably of five, six, or seven members.

The present invention is directed preferably to a method for inhibiting the premature polymerization of ethylenically unsaturated monomers comprising adding to said monomers an effective amount of a mixture comprising at least two different inhibitors having the structural formula:

wherein $R_1$ and $R_4$ are independently selected from the group consisting of hydrogen, alkyl, and heteroatom-substituted alkyl and $R_2$ and $R_3$ are independently selected from the group consisting of alkyl and heteroatom-substituted alkyl, and the portion represents the atoms necessary to form a five-, six-, or seven-membered heterocyclic ring. Such ring-completing atoms are preferably carbon atoms, but heteroatoms, such as O, N, P, or S, may also be present. It is preferred that one of the inhibitors be 4-amino-2,2,6,6-tetramethylpiperidinyloxy (i.e., 4-amino-TEMPO). As employed herein, the term "amino", where it is used to refer to an amino group in the 4-position of the TEMPO, is intended to include primary, secondary, and tertiary amino groups.

The effective amount of the combination of nitroxyl compounds is typically about 1 to 2,000 ppm, based on the weight of the ethylenically unsaturated monomer, although amounts outside this range may be appropriate depending upon the conditions of use. The amount of the combination of nitroxyl compounds is preferably about 5 to about 1,000 ppm, based on the weight of the ethylenically unsaturated monomer.

In another embodiment, the present invention is directed to a composition comprising:

(a) an ethylenically unsaturated monomer, and
(b) an effective inhibiting amount, to prevent premature polymerization of the ethylenically unsaturated monomer, of a mixture of at least two different inhibitors having the structural formula:

In this formula, $R_1$ and $R_4$ are independently selected from the group consisting of hydrogen, alkyl, and heteroatom-substituted alkyl and $R_2$ and $R_3$ are independently selected from the group consisting of alkyl and heteroatom-substituted alkyl; and $X_1$ and $X_2$ (1) are independently selected from the group consisting of halogen, cyano, $COOR_{11}$ (wherein $R_{11}$ is alkyl or aryl), amido, —S—$C_6H_5$, —S—$COCH_3$, —$OCOC_2H_5$, carbonyl, alkenyl, or alkyl of 1 to 15 carbon atoms, or (2) can be taken together to form a ring structure with the nitrogen, preferably of five, six, or seven members.

In a preferred embodiment, the present invention is directed to a composition comprising:

(a) an ethylenically unsaturated monomer, and
(b) an effective inhibiting amount, to prevent premature polymerization of the ethylenically unsaturated monomer, of a mixture of
(i) 1 to 99 percent by weight, based on the total weight of components (i) and (ii), of 4-amino-2,2,6,6-tetramethylpiperidinyloxy, wherein said amino group is a primary, secondary, or tertiary amino group, and, correspondingly,
(ii) 99 to 1 percent by weight of at least one other inhibitor having the structural formula:

wherein $R_1$ and $R_4$ are independently selected from the group consisting of hydrogen, alkyl, and heteroatom-substituted alkyl and $R_2$ and $R_3$ are independently selected from the group consisting of alkyl and heteroatom-substituted alkyl, and the portion represents the atoms necessary to form a five-, six-, or seven-membered heterocyclic ring.

The preferred amounts of components (i) and (ii) are 10 to 90 percent by weight of component (i) and, correspondingly, 90 to 10 percent by weight of component (s) (ii); more preferably, 20 to 80 percent by weight of component (i) and, correspondingly, 80 to 20 percent by weight of component(s) (ii); and most preferably, 20 to 50 percent by weight of component (i) and 50 to 80 percent by weight of component(s) (ii).

In a highly preferred embodiment, the present invention is directed to a method for inhibiting the premature polymerization of ethylenically unsaturated monomers comprising adding to said monomers from about 1 to about 2000 ppm, based on the weight of the ethylenically unsaturated monomer, of a mixture comprising

A) a first inhibitor comprising 4-amino-2,2,6,6-tetramethylpiperidinyloxy, wherein said amino group is a primary, secondary, or tertiary amino group; and
B) at least one other inhibitor having the structural formula:

wherein:
$R_1$ and $R_4$ are independently selected from the group consisting of hydrogen, alkyl, and heteroatom-substituted alkyl;
$R_2$ and $R_3$ are independently selected from the group consisting of alkyl and heteroatom-substituted alkyl;
$X_1$ and $X_2$ (1) are independently selected from the group consisting of alkyl groups of 1 to 15 carbon atoms or (2) taken together, form a ring structure with the nitrogen.

In another highly preferred embodiment the present invention is directed to a method for inhibiting the premature polymerization of ethylenically unsaturated monomers comprising adding to said monomers from about 1 to about 2000 ppm, based on the weight of the ethylenically unsaturated monomer, of a mixture comprising A) a first inhibitor comprising 4-amino-2,2,6,6-tetramethylpiperidinyloxy, wherein said amino group is a primary, secondary, or tertiary amino group; and
B) at least one other inhibitor having the structural formula:

wherein $R_1$ and $R_4$ are independently selected from the group consisting of hydrogen, alkyl, and heteroatom-substituted alkyl and $R_2$ and $R_3$ are independently selected from the group consisting of alkyl and heteroatom-substituted alkyl, and the portion represents the atoms necessary to form a five-, six-, or seven-membered heterocyclic ring.

In still another highly preferred embodiment the present invention is directed to a composition comprising:
 (a) an ethylenically unsaturated monomer, and
 (b) an effective inhibiting amount, to prevent premature polymerization of the ethylenically unsaturated monomer, in the range of from about 1 to about 2000 ppm, based on the weight of the ethylenically unsaturated monomer, of a mixture of
   (i) a first inhibitor comprising 4-amino-2,2,6,6-tetramethylpiperidinyloxy, wherein said amino group is a primary, secondary, or tertiary amino group; and
   (ii) at least one other inhibitor having the structural formula:

wherein:
 $R_1$ and $R_4$ are independently selected from the group consisting of hydrogen, alkyl, and heteroatom-substituted alkyl;
 $R_2$ and $R_3$ are independently selected from the group consisting of alkyl and heteroatom-substituted alkyl;
 $X_1$ and $X_2$ (1) are independently selected from the group consisting of alkyl of 1 to 15 carbon atoms or (2) taken together, form a ring structure with the nitrogen.

DESCRIPTION OF THE PREFERRED EMBODIMENTS

As stated above, in one preferred aspect, the present invention is directed to a method for inhibiting the premature polymerization of ethylenically unsaturated monomers comprising adding to said monomers an effective amount of a mixture comprising at least two different inhibitors having the structural formula:

wherein $R_1$ and $R_4$ are independently selected from the group consisting of hydrogen, alkyl, and heteroatom-substituted alkyl and $R_2$ and $R_3$ are independently selected from the group consisting of alkyl and heteroatom-substituted alkyl, and the portion represents the atoms necessary to form a five-, six-, or seven-membered heterocyclic ring wherein at least one of the inhibitors is 4-amino-TEMPO, wherein said amino group can be primary, secondary, or tertiary. Such ring-completing atoms are preferably carbon atoms, but heteroatoms, such as O, N, P, or S, may also be present.

Accordingly, one of the several classes of cyclic nitroxides that can be employed in combination with the 4-amino-TEMPO of the present invention can be represented by the following structural formula:

wherein $Z_1$, $Z_2$, and $Z_3$ are independently selected from the group consisting of oxygen, sulfur, secondary amines, tertiary amines, phosphorus of various oxidation states, and substituted or unsubstituted carbon atoms, such as $>CH_2$, $>CHCH_3$, $>C=O$, $>C(CH_3)_2$, $>CHBr$, $>CHCl$, $>CHI$, $>CHF$, $>CHOH$, $>CHCN$, $>C(OH)CN$, $>CHCOOH$, $>CHCOOCH_3$, $>CHCOOC_2H_5$, $>C(OH)COOC_2H_5$, $>C(OH)COOCH_3$, $>C(OH)CHOHC_2H_5$, $>CNR_5R_6$, $>CCONR_5R_6$, $>CH=NOH$, $>C=CH-C_6H_5$, $>CF_2$, $>CCl_2$, $>CBr_2$, $>CI_2$, $>CPR_{13}R_{14}R_{15}$, and the like, where $R_5$ and $R_6$ are independently selected from the group consisting of hydrogen, alkyl, aryl, and acyl, (provided that both $R_5$ and $R_6$ are not such that the second inhibitor is the same compound as the first inhibitor, i.e., 4-amino-TEMPO; it should be understood that it is intended that, for example, the first inhibitor could be 4-amino-TEMPO where the amino group is primary and the second inhibitor is 4-amino-TEMPO where the amino group is secondary or tertiary) and $R_{13}$, $R_{14}$, and $R_{15}$ are independently selected from the group consisting of unshared electrons, alkyl, aryl, =O, $OR_{16}$, and $NR_{17}R_{18}$, where $R_{16}$, $R_{17}$, and $R_{18}$ are independently selected from the group consisting of hydrogen, alkyl, and aryl. Where $R_5$ and/or $R_6$ are alkyl, it is preferred that they be a lower alkyl (i.e., one having one to four carbon atoms, e.g., methyl, ethyl, propyl, butyl, and isomers thereof).

Where $R_5$ and/or $R_6$ are aryl, it is preferred that they be aryl of from 6 to 10 carbon atoms, e.g., phenyl or naphthyl, which, in addition, may be substituted with non-interfering substituents, e.g., lower alkyl groups, halogens, and the like.

Where $R_5$ and/or $R_6$ are acyl, it is preferred that they be acyl of the structure where $R_7$ is alkyl, aryl, $OR_8$, or $NR_8R_9$ and where $R_8$ and $R_9$ are alkyl, aryl, or where $R_{10}$ is alkyl or aryl. Where $R_7$, $R_8$, $R_9$, or $R_{10}$ are alkyl, they are preferably alkyl of from 1 to 15 carbon atoms, more preferably lower alkyl of from 1 to 4 carbon atoms, as described above. Where $R_7$, $R_8$, $R_9$, or $R_{10}$ are aryl, they are preferably aryl of from 6 to 10 carbon atoms, as described above.

Another of the several classes of cyclic nitroxides that can be employed in the practice of the present invention can be represented by the following structural formula:

wherein $Z_1$ and $Z_2$, which may be the same or different, are nitrogen or substituted or unsubstituted carbon atoms, such as =C(H)—, =C(CH$_3$)—, =C(COOH)—, =C(COOCH$_3$)—, =C(COOC$_2$H$_5$)—, =C(OH)—, =C(CN)—, =C(NR$_5$R$_6$)—, =C(CONR$_5$R$_6$)—, and the like, and where $Z_3$, $R_5$, and $R_6$ are as described above.

The cyclic nitroxides employed in the practice of the present invention can also be derived from five-membered rings. These compounds are of the structure:

wherein $Z_2$ and $Z_3$, which may be the same or different, are sulfur, oxygen, secondary amines, tertiary amines, phosphorus of various oxidation states, or substituted or unsubstituted carbon atoms, such as >CH$_2$, >CHCH$_3$, >C=O, >C(CH$_3$)$_2$, >CHBr, >CHCl, >CHI, >CHF, >CHOH, >CHCN, >C(OH)CN, >CHCOOH, >CHCOOCH$_3$, >CHCOOC$_2$H$_5$, >C(OH)COOC$_2$H$_5$, >C(OH)COOCH$_3$, >C(OH)CHOHC$_2$H$_5$, >CNR$_5$R$_6$, >CCONR$_5$R$_6$, >CH=NOH, >C=CH—C$_6$H$_5$, CF$_2$, CCl$_2$, CBr$_2$, CI$_2$, >CPR$_{13}$R$_{14}$R$_{15}$, and the like, wherein the several R groups are as described above.

The cyclic nitroxides employed in the practice of the present invention can also have the structure:

wherein $Z_4$ and $Z_5$, which can be the same or different, can be nitrogen or a substituted or unsubstituted carbon atom, such as =C(H)—, =C(CH$_3$)—, =C(COOH)—, =C(COOCH$_3$)—, =C(COOC$_2$H$_5$)—, =C(OH)—, =C(CN)—, =C(NR$_5$R$_6$)—, =C(CONR$_5$R$_6$)—, and the like, where $R_5$ and $R_6$ are as described above.

Another class of cyclic nitroxides that can be employed in the practice of the present invention is of the structure:

wherein $Z_2$ and $Z_3$, which may be the same or different, are sulfur, oxygen, secondary amines, tertiary amines, or substituted or unsubstituted carbon atoms, such as >CH$_2$, >CHCH$_3$, >C=O, >C(CH$_3$)$_2$, >CHBr, >CHCl, >CHI, >CHF, >CHOH, >CHCN, >C(OH)CN, >CHCOOH, >CHCOOCH$_3$, >CHCOOC$_2$H$_5$, >C(OH)COOC$_2$H$_5$, >C(OH)COOCH$_3$, >C(OH)CHOHC$_2$H$_5$, >CNR$_5$R$_6$, >CCONR$_5$R$_6$, >CH=NOH, >C=CH—C$_6$H$_5$, CF$_2$, CCl$_2$, CBr$_2$, CI$_2$, and the like, where $R_5$ and $R_6$ are as described above.

Further, two or more nitroxyl groups can be present in the same molecule, for example, by being linked through one or more of the Z-type moieties by a linking group E, as disclosed in U.S. Pat. No. 5,254,760, which is incorporated herein by reference.

As stated above, $R_1$ and $R_4$ are independently selected from the group consisting of hydrogen, alkyl, and heteroatom-substituted alkyl, and $R_2$ and $R_3$ are independently selected from the group consisting of alkyl and heteroatom-substituted alkyl. The alkyl (or heteroatom-substituted) groups $R_1$ through $R_4$ can be the same or different and preferably contain 1 to 15 carbon atoms, e.g., methyl, ethyl, propyl, butyl, pentyl, hexyl, heptyl, octyl, nonyl, decyl, undecyl, dodecyl, tridecyl, tetradecyl, pentadecyl, and the like, and isomers thereof, e.g., t-butyl, 2-ethylhexyl, and the like. It is more preferred that $R_1$ through $R_4$ be lower alkyl (or heteroatom-substituted lower alkyl) of one to four carbon atoms (e.g., methyl, ethyl, propyl, butyl, and isomers thereof). Where heteroatom substituents are present, they can, for example, include halogen, oxygen, sulfur, nitrogen, and the like. It is most preferred that all of $R_1$ through $R_4$ be methyl.

Similarly, where $X_1$ and $X_2$ are alkyl, as mentioned above, they are preferably independently selected alkyl groups of from 1 to 15 carbon atoms. It is more preferred that $X_1$ and $X_2$ be independently selected lower alkyl groups of one to four carbon atoms (e.g., methyl, ethyl, propyl, butyl, and isomers thereof). It is most preferred that both $X_1$ and $X_2$ be methyl groups.

Examples of suitable nitroxide free radical compounds, that can be used as the second inhibitor in the practice of the present invention, include but are not limited to:
N,N-di-tert.-butyl nitroxide;
2,2,6,6-tetramethyl-piperidinyloxy;
4-amino-2,2,6,6-tetramethyl-piperidinyloxy;
4-(N-methylamino)-2,2,6,6-tetramethyl-piperidinyloxy;
4-(N-phenylamino)-2,2,6,6-tetramethyl-piperidinyloxy;
4-(N-benzylamino)-2,2,6,6-tetramethyl-piperidinyloxy;
4-hydroxy-2,2,6,6-tetramethyl-piperidinyloxy;
4-oxo-2,2,6,6-tetramethyl-piperidinyloxy;
4-(N,N-dimethylamino)-2,2,6,6-tetramethyl-piperidinyloxy;
4-(N,N-dibenzylamino)-2,2,6,6-tetramethyl-piperidinyloxy;
4-ethanoyloxy-2,2,6,6-tetramethyl-piperidinyloxy;
2,2,5,5-tetramethylpyrrolidinyloxy;
3-amino-2,2,5,5-tetramethylpyrrolidinyloxy;
2,2,4,4-tetramethyl-1-oxa-3-azacyclopentyl-3-oxy;
2,2,4,4-tetramethyl-1-oxa-3-pyrrolinyl-1-oxy-3-carboxylic acid;
2,2,3,3,5,5,6,6-octamethyl-1,4-diazacyclohexyl-1,4-dioxy;
4-bromo-2,2,6,6-tetramethyl-piperidinyloxy;
4-chloro-2,2,6,6-tetramethyl-piperidinyloxy;
4-iodo-2,2,6,6-tetramethyl-piperidinyloxy;
4-fluoro-2,2,6,6-tetramethyl-piperidinyloxy;
4-cyano-2,2,6,6-tetramethyl-piperidinyloxy;
4-carboxy-2,2,6,6-tetramethyl-piperidinyloxy;
4-carbomethoxy-2,2,6,6-tetramethyl-piperidinyloxy;
4-carbethoxy-2,2,6,6-tetramethyl-piperidinyloxy;
4-cyano-4-hydroxy-2,2,6,6-tetramethyl-piperidinyloxy;
4-methyl-2,2,6,6-tetramethyl-piperidinyloxy;
4-carbethoxy-4-hydroxy-2,2,6,6-tetramethyl-piperidinyloxy;
4-hydroxy-4-(1-hydroxypropyl)-2,2,6,6-tetramethyl-piperidinyloxy;
4-methyl-2,2,6,6-tetramethyl-1,2,5,6-tetrahydropyridine-1-oxyl;
4-carboxy-2,2,6,6-tetramethyl-1,2,5,6-tetrahydropyridine-1-oxyl;
4-carbomethoxy-2,2,6,6-tetramethyl-1,2,5,6-tetrahydropyridine-1-oxyl;
4-carbethoxy-2,2,6,6-tetramethyl-1,2,5,6-tetrahydropyridine-1-oxyl;
4-amino-2,2,6,6-tetramethyl-1,2,5,6-tetrahydropyridine-1-oxyl;
4-amido-2,2,6,6-tetramethyl-1,2,5,6-tetrahydropyridine-1-oxyl;
3,4-diketo-2,2,5,5-tetramethylpyrrolidinyloxy;
3-keto-4-oximino-2,2,5,5-tetramethylpyrrolidinyloxy;
3-keto-4-benzylidine-2,2,5,5-tetramethylpyrrolidinyloxy;
3-keto-4,4-dibromo-2,2,5,5-tetramethylpyrrolidinyloxy;
2,2,3,3,5,5-hexamethylpyrrolidinyloxy;
3-carboximido-2,2,5,5-tetramethylpyrrolidinyloxy;
3-oximino-2,2,5,5-tetramethylpyrrolidinyloxy;
3-hydroxy-2,2,5,5-tetramethylpyrrolidinyloxy;
3-cyano-3-hydroxy-2,2,5,5-tetramethylpyrrolidinyloxy;
3-carbomethoxy-3-hydroxy-2,2,5,5-tetramethylpyrrolidinyloxy;
3-carbethoxy-3-hydroxy-2,2,5,5-tetramethylpyrrolidinyloxy;
2,2,5,5-tetramethyl-3-carboxamido-2,5-dihydropyrrole-1-oxyl;
2,2,5,5-tetramethyl-3-amino-2,5-dihydropyrrole-1-oxyl;
2,2,5,5-tetramethyl-3-carbethoxy-2,5-dihydropyrrole-1-oxyl;
2,2,5,5-tetramethyl-3-cyano-2,5-dihydropyrrole-1-oxyl;
bis(1-oxyl-2,2,6,6-tetramethylpiperidin-4-yl)succinate;
bis(1-oxyl-2,2,6,6-tetramethylpiperidin-4-yl)adipate;
bis(1-oxyl-2,2,6,6-tetramethylpiperidin-4-yl)sebacate;
bis(1-oxyl-2,2,6,6-tetramethylpiperidin-4-yl)$_n$-butylmalonate;
bis(1-oxyl-2,2,6,6-tetramethylpiperidin-4-yl)phthalate;
bis(1-oxyl-2,2,6,6-tetramethylpiperidin-4-yl)isophthalate;
bis(1-oxyl-2,2,6,6-tetramethylpiperidin-4-yl)terephthalate;
bis(1-oxyl-2,2,6,6-tetramethylpiperidin-4-yl) hexahydroterephthalate;
N,N'-bis(1-oxyl-2,2,6,6-tetramethylpiperidin-4-yl) adipamide;
N-(1-oxyl-2,2,6,6-tetramethylpiperidin-4-yl)-caprolactam;
N-(1-oxyl-2,2,6,6-tetramethylpiperidin-4-yl)-dodecylsuccinimide;
2,4,6-tris-[N-butyl-N-(1-oxyl-2,2,6,6-tetramethylpiperidin-4-yl)]-s-triazine;
4,4'-ethylenebis(1-oxyl-2,2,6,6-tetramethylpiperazin-3-one);
and the like.

One inhibitor of the combination will be 4-amino-2,2,6,6-tetramethyl-piperidinyloxy, 4-(N-alkylamino)-2,2,6,6-tetramethyl-piperidinyloxy, or 4-(N,N-dialkylamino)-2,2,6,6-tetramethyl-piperidinyloxy (all of which are referred to herein as 4-amino-TEMPO). It is further preferred that the other inhibitor be 4-oxo-2,2,6,6-tetramethylpiperidinyloxy; N,N-di-tert.-butyl nitroxide, 2,2,6,6-tetramethyl-piperidinyloxy; 4-hydroxy-2,2,6,6-tetramethyl-piperidinyloxy; or a 4-amino-TEMPO that is different from the first inhibitor.

Such stable nitroxide free radical compounds can be prepared by known methods. (See, for example, U.S. Pat. Nos. 3,163,677; 3,334,103; 3,372,182; 3,422,144; 3,494,930; 3,502,692; 3,873,564; 3,966,711; and 4,665,185; which are incorporated herein by reference.) They are suitable for use over a wide range of temperatures, but distillation temperatures employed with the ethylenically unsaturated monomers that are stabilized by the process of the present invention typically range from about 60° C. to about 180° C., preferably from about 70° C. to about 165° C., and, more preferably, from about 80° C. to about 150° C. Such distillations are generally performed at an absolute pressure in the range of about 10 to about 1,200 mm of Hg.

The ethylenically unsaturated monomer, the premature polymerization of which is an object of the present invention, can be any such monomer for which unintended polymerization during its manufacture, storage, and/or distribution is a problem. Among those monomers that will benefit from the practice of the present invention are: styrene, α-methylstyrene, styrene sulfonic acid, vinyltoluene, divinylbenzenes, polyvinylbenzenes, alkylated styrene, 2-vinylpyridine, acrylonitrile, methacrylonitrile, methyl acrylate, ethyl acrylate, methyl methacrylate, ethyl methacrylate, acrylic acid, methacrylic acid, butadiene, chloroprene, isoprene, and the like.

The ethylenically unsaturated monomers will not necessarily be stabilized indefinitely by the presence of the inhibitor blend, especially when the monomers are heated as in distillation, but they can be considered to be stabilized as long as there is a measurable increase in the time for which they can be heated before the onset of polymerization.

Those skilled in the art will understand that, if desired, additional free radical scavengers can be included in the stabilized compositions and the methods for preparing them that are the subject of the present invention. For example, air or $O_2$, as disclosed in U.S. Pat. Nos. 5,545,782 and 5,545, 786, can be added, as can the aromatic nitro compounds disclosed in U.S. Pat. No. 5,254,760, the dihetero-substituted benzene compounds having at least one transferable hydrogen, e.g., a quinone derivative, such as the mono-methyl-ether of hydroquinone disclosed in European Patent Application 0 765 856 A1, the iron compounds disclosed in WO98/25872, and other inhibitors, e.g., phenolics and certain inorganic salts, well known to those skilled in the art.

The polymerization inhibitor composition can be introduced into the monomer to be protected by any conventional method. It can be added as a concentrated solution in suitable solvents just upstream from the point of desired application by any suitable means. In addition, the individual inhibiting components can be injected separately into the distillation train along with the incoming feed or through separate entry points, provided there is an efficient distribution of the inhibitors. Since the inhibitors are gradually depleted during the distillation operation, it is generally advantageous to maintain the appropriate amount of the inhibitor mixture in the distillation apparatus by adding inhibitors during the course of the distillation process. Adding inhibitors can be done either on a generally continuous basis or intermittently, in order to maintain the concentration of inhibitor mixture above the minimum required level.

The advantages and the important features of the present invention will be more apparent from the following examples.

EXAMPLES

Procedure for Dynamic Reboiler Test with Feed Shut-Off

Preparation of Feed Solution.

T-Butylcatechol (TBC) is removed from commercially available styrene by distillation under vacuum. Removal of TBC is verified by caustic titration. The desired amount of inhibitor(s) is added to this TBC-free styrene either directly or by first making a concentrated solution of the inhibitor in TBC-free styrene followed by further dilution with TBC-free styrene.

Procedure for Dynamic Reboiler Test.

A quantity of the Feed Solution containing inhibitor (blend) at the desired charge (stated as a wt/wt total inhibitor to styrene) is added to a round-bottom flask (the "Pot") and heated to the desired temperature (usually 116° C.) and brought to reflux by adjusting the pressure/vacuum. Once the Pot contents are at temperature, a continuous stream of fresh Feed Solution is begun at a rate that will add the volume of the initial Pot solution to the Pot over a period of time called the residence time (typically one hour). At the same time that the fresh Feed Solution flow is begun, the Bottoms Stream flow is also begun. The Bottoms Stream is solution in the Pot that is removed at the same rate as the fresh Feed Solution is added. The equal flows of Feed and Bottoms streams cause the quantity in the Pot to remain constant over the time of the experiment while allowing continuous replenishment of inhibitor. This procedure simulates the way inhibitors are used in a distillation train of a plant producing vinyl monomers. The experiment continues with flow in and out of the Pot for a specified period of time, typically six or seven hours. Samples are collected hourly from the Bottoms Stream. These samples are analyzed for polymer content via the methanol turbidity method. The amount of polymer in the samples is an indication of effectiveness of the inhibitor being tested.

Procedure for Feed Shut-Off.

At the end of the Reboiler Test Run (typically six or seven hours), a sample is collected from the Bottoms Stream. This sample corresponds to Feed Shut-Off Time=0 minutes. The flows of fresh Feed Solution and Bottoms Stream are stopped. The vacuum and temperature are monitored and adjusted to maintain boiling at the desired temperature of the experiment. Samples are periodically removed from the Pot (typically every five or ten minutes). These samples are analyzed for polymer content via the methanol turbidity method. Data during this time are used to generate the "Feed Shut-Off Curve" for the run.

A less steep slope in the Feed Shut-Off Curve (slower rate of polymer production over time) indicates a more effective inhibiting system in the event of a loss of feed in the plant. A longer period of time before initiation of significant polymer formation is also an indication of a more effective inhibiting system in the event of a loss of feed in the plant. A preferred system will have a long delay prior to initiation of polymer formation followed by a slow rate of polymer production once initiated.

Example 1

Figure 1:
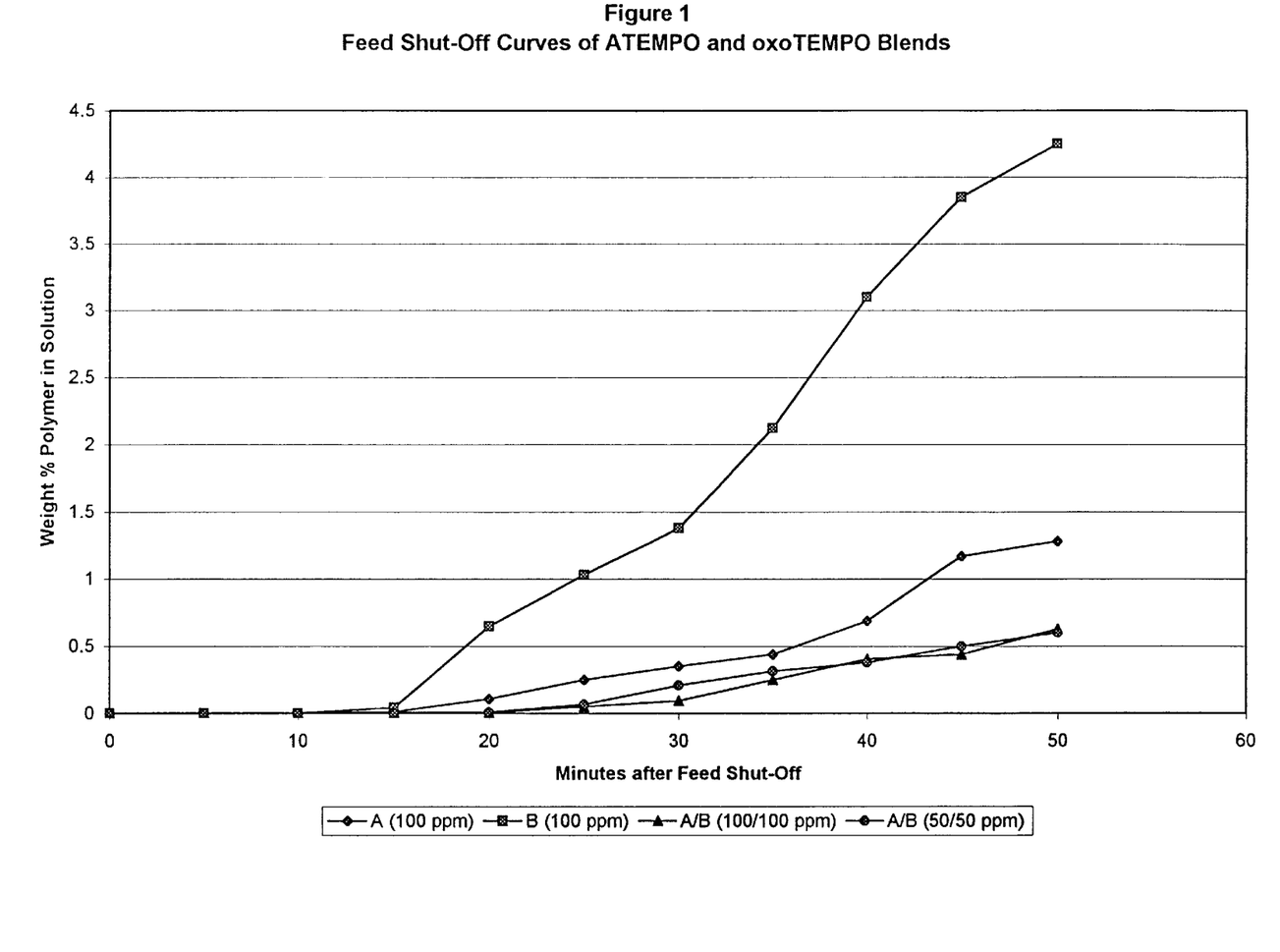
FIG. 1 is a graph showing the slow rate of polymerization of the compositions of the present invention after the shutoff of feed in a steady state dynamic testing system, as compared with the rates provided by the individual species, wherein the species and compositions comprise 4-amino-TEMPO, 4-oxo-TEMPO, and combinations thereof as the inhibitor(s).

The above procedure is carried out using 4-amino-TEMPO (in this case, 4-amino-2,2,6,6-tetramethyl-piperidinyloxy), 4-oxo-TEMPO, and combinations thereof as the inhibitor(s). The results are shown in FIG. 1 and clearly indicate the synergistic improvement that is realized by employing a combination of the two nitroxide compounds, as opposed to an equal quantity of either one alone. The data for the graph of FIG. 1 are shown in Table 1.

TABLE 1

Reboiler Run with 4-Amino-TEMPO, 4-Oxo-TEMPO, and Blends 116° C. (% Polymer)

| | A (100 ppm) | B (100 ppm) | A/B (100/100 ppm) | A/B (50/50 ppm) |
|---|---|---|---|---|
| Time (Hours) | | | | |
| 0 | 0 | 0 | 0 | |
| 2 | 0.0003 | 0.0013 | 0.0003 | 0.0007 |
| 3 | 0.00037 | 0.0011 | 0.00027 | 0.00043 |
| 4 | 0.0004 | 0.0013 | 0.00037 | 0.0005 |
| 5 | 0.00046 | 0.0017 | 0.0005 | 0.0007 |
| 6 | 0.00049 | 0.0017 | 0.0006 | 0.0006 |
| 7 | 0.00052 | 0.0017 | 0.0007 | 0.00065 |
| Time (min.-F/SO) | | | | |
| 0 | 0 | 0 | 0 | 0 |
| 5 | 0.00064 | 0.0024 | 0.0008 | 0.0007 |
| 10 | 0.0004 | 0.0024 | 0.0009 | 0.00074 |
| 15 | 0.0135 | 0.043 | 0.0052 | 0.001 |
| 20 | 0.108 | 0.65 | 0.0064 | 0.011 |
| 25 | 0.25 | 1.03 | 0.049 | 0.069 |
| 30 | 0.35 | 1.38 | 0.095 | 0.208 |
| 35 | 0.44 | 2.12 | 0.25 | 0.315 |
| 40 | 0.69 | 3.1 | 0.405 | 0.38 |
| 45 | 1.17 | 3.85 | 0.44 | 0.5 |
| 50 | 1.28 | 4.25 | 0.63 | 0.6 |
| 55 | — | — | — | 0.7 |
| 60 | — | — | — | 0.68 |
| 65 | — | — | — | 0.86 |

A is 4-amino-TEMPO
B is 4-oxo-TEMPO
F/SO is Feed Shut-Off

Example 2

Figure 2:
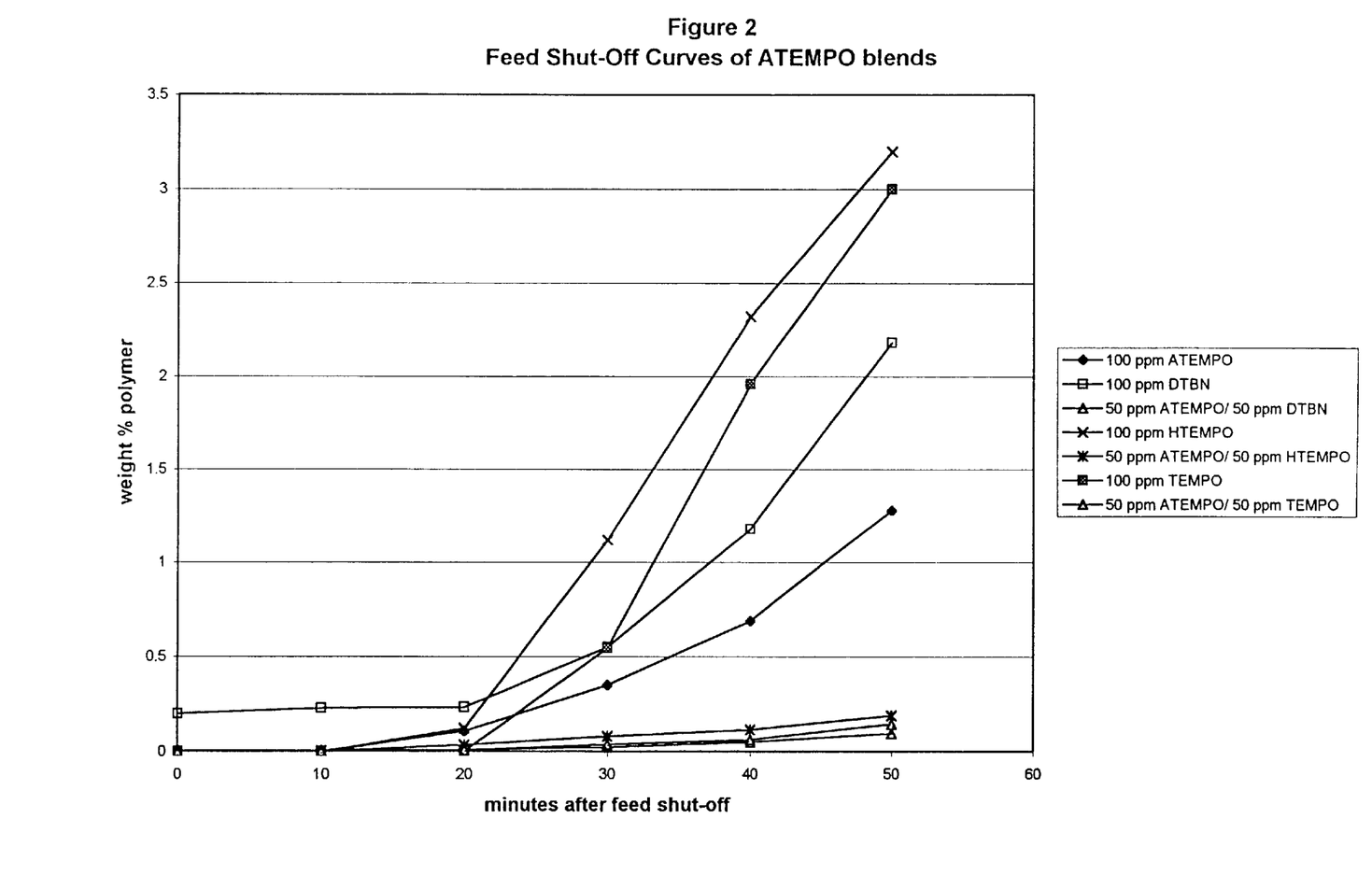
FIG. 2 is a graph showing the slow rate of polymerization of the compositions of the present invention after the shutoff of feed in a steady state dynamic testing system, as compared with the rates provided by the individual species, wherein the species and compositions comprise 4-amino-TEMPO, DTBN, HTEMPO, and TEMPO, and combinations thereof as the inhibitor(s).

The above procedure was carried out using 4-amino-TEMPO (in this case, 4-amino-2,2,6,6-tetramethyl-piperidinyloxy), DTBN (N,N-di-tert-butylnitroxide), HTEMPO (4-hydroxy-TEMPO), and TEMPO (2,2,6,6-tetramethylpiperidin-1-oxyl) and combinations thereof as the inhibitor(s). The results are shown in FIG. 2 and clearly indicate the synergistic improvement that is realized by employing a combination of the two nitroxide compounds, one of which is 4-amino-TEMPO, as opposed to an equal quantity of either one alone. The data for the graph of FIG. 2 are shown in Table 2.

Example 3

Figure 3:
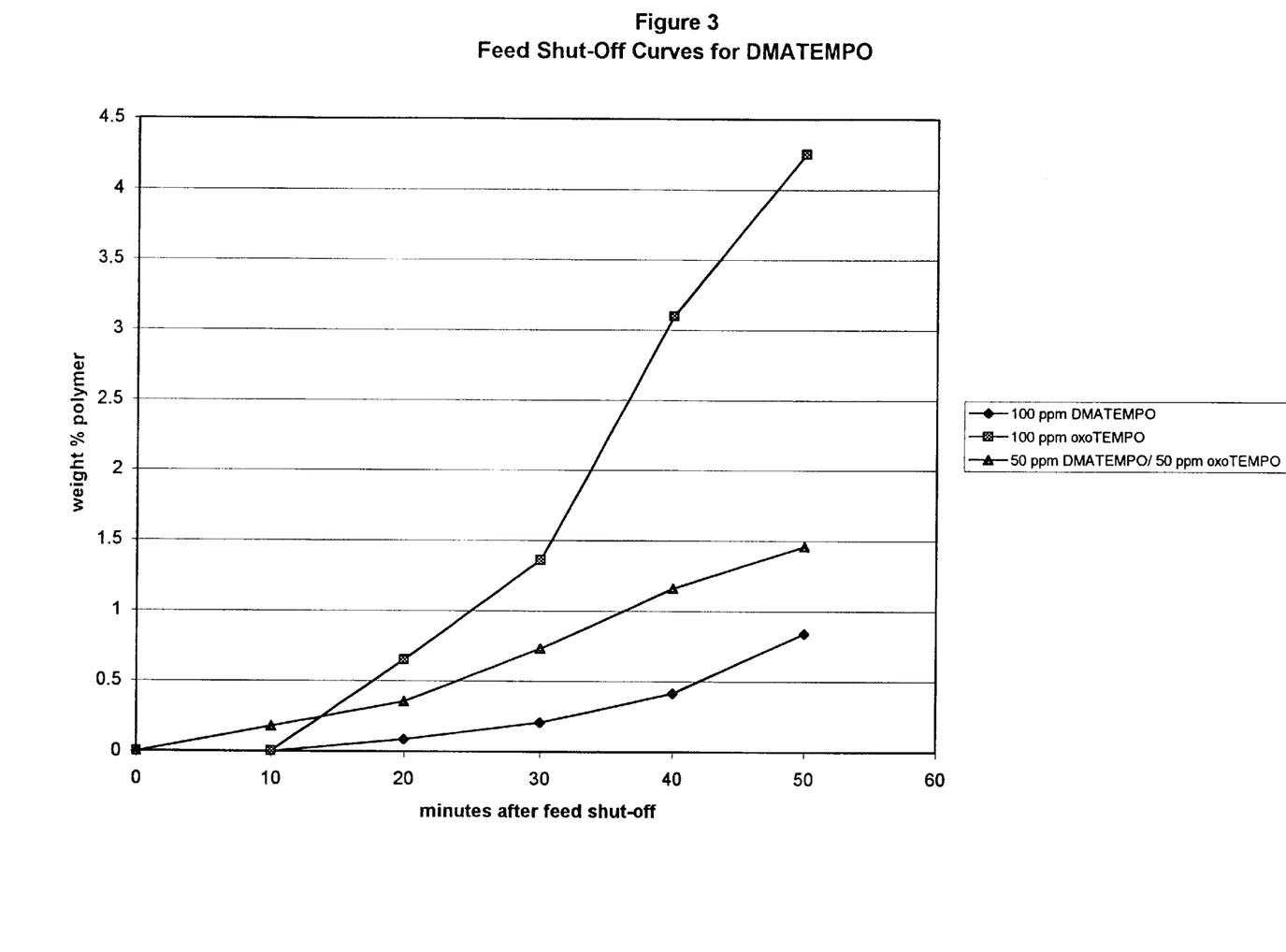
FIG. 3 is a graph showing the slow rate of polymerization of the compositions of the present invention after the shutoff of feed in a steady state dynamic testing system, as compared with the rates provided by the individual species, wherein the species and compositions comprise DMATEMPO, 4-oxo-TEMPO, and combinations thereof as the inhibitor(s).

The above procedure is repeated using DMATEMPO (4-(N,N-dimethylamino)-TEMPO, 4-oxo-TEMPO, and a combination thereof as the inhibitor(s). The results are shown in FIG. 3 and indicate the synergistic improvement that is realized by employing a combination of these two nitroxide compounds, as opposed to an equal quantity of either one alone. The data for the graph of FIG. 3 are shown in Table 3.

TABLE 2

|  | 100 ppm ATEMPO | 100 ppm DTBN | 50 ppm ATEMPO/50 ppm DTBN | 100 ppm HTEMPO | 50 ppm ATEMPO/50 ppm HTEMPO | 100 ppm TEMPO | 50 ppm ATEMPO/50 ppm HTEMPO |
| --- | --- | --- | --- | --- | --- | --- | --- |
| Hour |  |  |  |  |  |  |  |
| 2 | 0.0003 | 0.134 | 0.00022 | 0.00038 | 0.00014 | 0.00025 | 0.0002 |
| 3 | 0.00037 | 0.174 | 0.00312 | 0.00068 | 0.00014 | 0.00024 | 0.00014 |
| 4 | 0.0004 | 0.164 | 0.00145 | 0.001 | 0.0002 | 0.00024 | 0.00017 |
| 5 | 0.00046 | 0.15 | 0.00385 | 0.0012 | 0.00024 | 0.0003 | 0.00016 |
| 6 | 0.00049 | 0.198 | 0.00375 | 0.0012 | 0.00034 | 0.0004 | 0.00021 |
| Mins. after feed shut-off |  |  |  |  |  |  |  |
| 0 | 0.0005 | 0.198 | 0.0038 | 0.0012 | 0.00034 | 0.00037 | 0.00021 |
| 10 | 0.0004 | 0.230 | 0.0058 | 0.0012 | 0.0014 | 0.00044 | 0.00027 |
| 20 | 0.108 | 0.235 | 0.0088 | 0.123 | 0.035 | 0.0013 | 0.0074 |
| 30 | 0.35 | 0.55 | 0.023 | 1.12 | 0.08 | 0.545 | 0.037 |
| 40 | 0.69 | 1.18 | 0.05 | 2.32 | 0.114 | 1.96 | 0.062 |
| 50 | 1.28 | 2.18 | 0.094 | 3.2 | 0.19 | 3 | 0.144 |

TABLE 3

| Mins. after feed shut-off | 100 ppm DMATEMPO | 100 ppm oxoTEMPO | 50 ppm DMATEMPO/50 ppm oxoTEMPO |
| --- | --- | --- | --- |
| 0 | 0.00042 | 0.0017 | 0.00068 |
| 10 | 0.00044 | 0.0024 | 0.18 |
| 20 | 0.085 | 0.65 | 0.355 |
| 30 | 0.208 | 1.358 | 0.73 |
| 40 | 0.415 | 3.1 | 1.16 |
| 50 | 0.84 | 4.25 | 1.46 |

In view of the many changes and modifications that can be made without departing from principles underlying the invention, reference should be made to the appended claims for an understanding of the scope of the protection to be afforded the invention.

What is claimed is:

1. A method for inhibiting the premature polymerization of vinyl aromatic monomers selected from the group consisting of styrene, α-methylstyrene, styrene sulfonic acid, vinyltoluene, divinylbenzenes, polyvinylbenzenes, alkylated styrene and 2-vinylpyridine comprising adding to said monomers a polymerization inhibiting amount of a mixture comprising.

A) a first inhibitor comprising 4-amino-2,2,6,6-tetramethylpiperidinyloxy, wherein said amino group is a primary, secondary, or tertiary amino group; and B) at least one other inhibitor having the structural formula:

wherein:

$R_1$ and $R_4$ are independently selected from the group consisting of hydrogen, alkyl, and heteroatom-substituted alkyl;

$R_2$ and $R_3$ are independently selected from the group consisting of alkyl and heteroatom-substituted alkyl;

$X_1$ and $X_2$ (1) are independently selected alkyl groups of 1 to 15 carbon atoms or (2) taken together, form a ring structure with the nitrogen.

2. The method of claim 1 wherein the inhibitors are employed in an amount of from about 1 to about 2000 ppm, based on the weight of the vinyl aromatic monomer.

3. A method for inhibiting the premature polymerization of vinyl aromatic monomers selected from the group consisting of styrene, α-methylstyrene, styrene sulfonic acid, vinyltoluene, divinylbenzenes, polyvinylbenzenes, alkylated styrene and 2-vinylpyridine comprising adding to said monomers a polymerization inhibiting amount of a mixture comprising A) a first inhibitor comprising 4-amino-2,2,6,6-tetramethylpiperidinyloxy, wherein said amino group is a primary, secondary, or tertiary amino group; and B) at least one other inhibitor having the structural formula:

wherein $R_1$ and $R_4$ are independently selected from the group consisting of hydrogen, alkyl, and heteroatom-substituted alkyl and $R_2$ and $R_3$ are independently selected from the group consisting of alkyl and heteroatom-substituted alkyl, and the portion represents the atoms necessary to form a five-, six-, or seven-membered heterocyclic ring.

4. The method of claim 3 wherein the inhibitors are employed in an amount of from about 1 to about 2000 ppm, based on the weight of the vinyl aromatic monomer.

5. The method of claim 1 wherein at least one of the inhibitors B) is selected from the group consisting of 4-oxo-2,2,6,6-tetramethyl-1-piperidinyloxy ; 4-hydroxy-2,2,6,6-tetramethyl-1-piperidinyloxy; 2,2,6,6-tetramethyl-1-piperidinyloxy;N,N-di-tert-butylnitroxide; and a 4-amino-2,2,6,6-tetramethylpiperidinyloxy, wherein said amino group is a primary, secondary, or tertiary amino group that is different from the amino group of the first inhibitor.

6. The method of claim 1 wherein the vinyl aromatic monomer is styrene.

7. The method of claim 6 wherein at least one of the inhibitors B) is selected from the group consisting of 4-oxo-2,2,6,6-tetramethyl-1-piperidinyloxy ; 4-hydroxy-2,2,6,6-tetramethyl-1-piperidinyloxy; 2 ,2,6,6-tetramethyl-1-piperidinyloxy; N,N-di-tert-butylnitroxide; and a 4-amino-2,2,6,6-tetramethylpiperidinyloxy, wherein said amino group is a primary, secondary, or tertiary amino group, that is different from the first inhibitor.

8. The method of claim 3 wherein the vinyl aromatic monomer is styrene.

9. The method of claim 8 wherein at least one of the inhibitors B) is selected from the group consisting of 4-oxo-2,2,6,6-tetramethyl-1-piperidinyloxy ; 4-hydroxy-2,2,6,6-tetramethyl-1-piperidinyloxy; 2,2,6,6-tetramethyl-1-piperidinyloxy; N,N-di-tert-butylnitroxide; and a 4-amino-2,2,6,6-tetramethylpiperidinyloxy, wherein said amino group is a primary, secondary, or tertiary amino group, that is different from the amino group of the first inhibitor.

10. A composition comprising:
(a) a vinyl aromatic monomer selected from the group consisting of styrene, α-methylstvrene, styrene sulfonic acid, vinyltoluene, divinylbenzenes, polyvinylbenzenes, alkylated styrene and 2-vinvipyridine and
(b) an effective inhibiting amount, to prevent premature polymerization of the vinyl aromatic monomer, of a mixture of
(i) a first inhibitor comprising 4-amino-2,2,6,6-tetramethylpiperidinyloxy, wherein said amino group is a primary, secondary, or tertiary amino group; and
(ii) at least one other inhibitor having the structural formula:

wherein:
$R_1$ and $R_4$ are independently selected from the group consisting of hydrogen, alkyl, and heteroatom-substituted alkyl;
$R_2$ and $R_3$ are independently selected from the group consisting of alkyl and heteroatom-substituted alkyl;
$X_1$ and $X_2$ (1) are independently selected alkyl groups of 1 to 15 carbon atoms or (2) taken together, form a ring structure with the nitrogen.

11. The composition of claim 10 wherein the inhibitors are present in an amount of from about 1 to about 2000 ppm, based on the weight of the vinyl aromatic monomer.

12. The composition of claim 10 wherein at least one of the inhibitors B) is selected from the group consisting of 4-oxo-2,2,6,6-tetramethyl-1-piperidinyloxy; 4-hydroxy-2,2,6,6-tetramethyl-1-piperidinyloxy; 2,2,6,6-tetramethyl-1-piperidinyloxy; N,N-di-tert-butylnitroxide; and a 4-amino-2,2,6,6-tetramethylpiperidinyloxy, wherein said amino group is a primary, secondary, or tertiary amino group, that is different from the amino group of the first inhibitor.

13. The composition of claim 10 wherein the vinyl aromatic monomer is styrene.

14. The composition of claim 13 wherein at least one of the inhibitors B) is selected from the group consisting of 4-oxo-2,2,6,6-tetramethyl-1-piperidinyloxy ; 4-hydroxy-2,2,6,6-tetramethyl-1-piperidinyloxy; 2,2,6,6-tetramethyl-1-piperidinyloxy; N,N-di-tert-butylnitroxide; and a 4-amino-2,2,6,6-tetramethylpiperidinyloxy, wherein said amino group is a primary, secondary, or tertiary amino group, that is different from the amino group of the first inhibitor.

15. A composition comprising:
(a) a vinyl aromatic monomer selected from the group consisting of styrene, α-methylstyrene, styrene sulfonic acid, vinyltoluene, divinylbenzenes, polyvinylbenzenes, alkylated styrene and 2-vinvipyridine, and
(b) an effective inhibiting amount, to prevent premature polymerization of the vinyl aromatic monomer, of a mixture of
(i) 1 to 99 percent by weight, based on the total weight of components (i) and (ii), of a first inhibitor comprising 4-amino-2,2,6,6-tetramethylpiperidinyloxy, wherein said amino group is a primary, secondary, or tertiary amino group, and, correspondingly,
(ii) 99 to 1 percent by weight of at least one other inhibitor having the structural formula:

wherein $R_1$ and $R_4$ are independently selected from the group consisting of hydrogen, alkyl, and heteroatom-substituted alkyl and $R_2$ and $R_3$ are independently selected from the group consisting of alkyl and heteroatom-substituted alkyl, and the portion represents the atoms necessary to form a five-, six-, or seven-membered heterocyclic ring.

16. The composition of claim 15 wherein the inhibitors are present in an amount of from about 1 to about 2000 ppm, based on the weight of the vinyl aromatic monomer.

17. The composition of claim 16 wherein the vinyl aromatic monomer is styrene.

* * * * *